(12) United States Patent
Boivin et al.

(10) Patent No.: US 10,806,519 B2
(45) Date of Patent: Oct. 20, 2020

(54) COMPUTER-ASSISTED SURGERY SYSTEM WITH USER INTERFACE TOOL USED AS MOUSE IN STERILE SURGERY ENVIRONMENT

(75) Inventors: Michel Boivin, Montréal (CA); Bruno Falardeau, Verdun (CA); Franck Maras, Montréal (CA); Simon Ferron-Forget, Montréal (CA); François Paradis, Boucherville (CA); Pierre T. A.-Nguyen, Montréal (CA)

(73) Assignee: ORTHOSOFT ULC, Montreal (CA)

( * ) Notice: Subject to any disclaimer, the term of this patent is extended or adjusted under 35 U.S.C. 154(b) by 583 days.

(21) Appl. No.: 12/144,198

(22) Filed: Jun. 23, 2008

(65) Prior Publication Data

US 2008/0319313 A1 Dec. 25, 2008

Related U.S. Application Data

(60) Provisional application No. 60/945,626, filed on Jun. 22, 2007.

(51) Int. Cl.
*A61B 34/20* (2016.01)
*A61B 34/00* (2016.01)
*A61B 34/10* (2016.01)

(52) U.S. Cl.
CPC ........ *A61B 34/20* (2016.02); *A61B 2034/101* (2016.02); *A61B 2034/102* (2016.02); *A61B 2034/2055* (2016.02); *A61B 2034/2068* (2016.02); *A61B 2034/256* (2016.02)

(58) Field of Classification Search
CPC ............................ A61B 19/5244; A61B 17/00
USPC ........................................................ 600/407
See application file for complete search history.

(56) References Cited

U.S. PATENT DOCUMENTS

| | | | |
|---|---|---|---|
| 5,230,623 A | * | 7/1993 | Guthrie ................ G06F 3/0346 33/513 |
| 5,971,997 A | | 10/1999 | Guthrie et al. |
| 7,663,509 B2 | * | 2/2010 | Shen .............................. 341/20 |
| 2004/0193413 A1 | | 9/2004 | Wilson et al. |
| 2005/0197569 A1 | * | 9/2005 | McCombs ................... 600/426 |
| 2005/0228266 A1 | | 10/2005 | McCombs |
| 2005/0281465 A1 | | 12/2005 | Marquart et al. |
| 2006/0036947 A1 | | 2/2006 | Jelley et al. |

(Continued)

FOREIGN PATENT DOCUMENTS

WO 2004070581 A2 8/2004
WO WO-2004/107959 12/2004

(Continued)

*Primary Examiner* — Serkan Akar
(74) *Attorney, Agent, or Firm* — Norton Rose Fulbright Canada LLP

(57) ABSTRACT

A method for establishing an interaction between an operator and a monitor of a computer-assisted surgery system comprises tracking a tool manipulated by the operator for providing surgical data calculated from the position/orientation of the tool. A desired interaction is identified from the operator by tracking the tool reaching a specific position and/or a specific orientation. An interactive action is activated on a monitor as a function of the desired interaction, the interactive action being unrelated to said surgical data. A motion of the tool is converted to additional interactions related to said interactive action. A computer-assisted surgery system is also provided.

17 Claims, 4 Drawing Sheets

(56) References Cited

U.S. PATENT DOCUMENTS

2006/0173264 A1\* 8/2006 Jansen .................. A61B 34/74
                                                      600/407
2006/0200025 A1   9/2006 Elliott et al.
2007/0016008 A1   1/2007 Schoenfeld
2007/0073137 A1\* 3/2007 Schoenefeld .......... A61B 90/36
2007/0118400 A1   5/2007 Morita et al.
2008/0084392 A1\* 4/2008 Potenzone ................... 345/166
2008/0268931 A1\* 10/2008 Alderucci ........... G07F 17/3209
                                                      463/11

FOREIGN PATENT DOCUMENTS

| WO | 2005001679 A1 | 1/2005 |
| WO | WO-2005/092230 | 10/2005 |
| WO | WO-2007/059965 | 5/2007 |
| WO | WO-2007/137093 | 11/2007 |

\* cited by examiner

US 10,806,519 B2

COMPUTER-ASSISTED SURGERY SYSTEM WITH USER INTERFACE TOOL USED AS MOUSE IN STERILE SURGERY ENVIRONMENT

CROSS-REFERENCE TO RELATED APPLICATION

The present application claims priority on U.S. Provisional Patent Application No. 60/945,626, filed on Jun. 22, 2007.

FIELD OF THE APPLICATION

The present application generally relates to optical tracking systems and, more particularly but not exclusively, to interactions between a tool operator and a tracking system.

BACKGROUND OF THE ART

There are many advantages to being able to operate a computer-aided surgery (CAS) system in an operating room. For a system that allows real-time display of the relative positions of three-dimensional models of anatomical structures and of a surgical tool by tracking of the latter, this means being able to select a component or section of an image displayed on a monitor and perform operations on it, such as zooming in and out, rotating it, etc. It also means enabling a surgeon to digitize points, whereby the latter may, for instance, define a profile of an operated bodily part. Moreover, CAS systems provide real-time calculated data to the operator, including angles, distances, orientations, etc.

The interaction between the surgeon and the CAS system presents some difficulties. For one thing, the surgeon operates in a sterile zone, whereas components of the CAS system are in a non-sterile zone. To perform some computer-related operations, such as controlling the monitor displays, the surgeon is required to interact with the CAS system. For instance, the act of selecting an object on a screen is typically done with a computer mouse, the mouse directing a visible cursor to the desired point on the image. However, due to the need for all objects in the sterile zone of the operating room to be sterile, a mouse cannot readily be used in the sterile zone to perform such actions.

It is possible to have a person other than the surgeon interacting with the CAS system. In this case, the surgeon, or other person manipulating a surgical tool, needs to verbalize specific instructions to the person interacting with the CAS system in order to obtain the desired results. Another known way to interact with a CAS system is to use a keypad in a sterile bag. These techniques are both tedious and inefficient.

U.S. Publication No. 2007/0073137, by Schoenfeld, describes a virtual mouse for use in surgical navigation. The virtual mouse involves a probe and an input pad, both tracked by the CAS system. The CAS system, therefore, interprets movements of the probe on the input pad as movements of the virtual mouse, thereby resulting in actions on the monitors (e.g., movements of an on-screen pointer). In order to simulate mouse clicks, the optical markers are occluded or blocked, and the CAS system recognizes such selective gesturing as a trigger.

SUMMARY OF THE APPLICATION

It is therefore an aim of the present invention to provide a novel system with user interface in computer-assisted surgery.

It is a further aim of the present invention to provide a novel method for establishing an interaction between an operator and a CAS monitor.

Therefore, in accordance with the present application, there is provided a method for establishing an interaction between an operator and a monitor of a computer-assisted surgery system, comprising: tracking a tool manipulated by the operator for providing surgical data calculated from the position/orientation of the tool; identifying a desired interaction from the operator by tracking the tool reaching at least one of a specific position and a specific orientation; activating an interactive action on a monitor as a function of the desired interaction, the interactive action being unrelated to said surgical data; and converting a motion of the tool to additional interactions related to said interactive action.

Further in accordance with the present application, there is provided a computer-assisted surgery system comprising: a tool having a trackable reference so as to be tracked for position; a sensor device for tracking of the tool; a computer-assisted surgery processing unit having: a position/orientation calculator for determining at least one of a position and an orientation of the tool for the processing unit to output surgical data as a function of the position of the tool; a desired interaction detector for monitoring at least one of the position and the orientation of the tool, and to send a detection signal to the processing unit when the tool is in at least one of a specific position and a specific orientation; a monitor for displaying a graphical user interface, the graphical user interface activating a selection pointer or triggering an action unrelated to said surgical data when the tool is in said specific position and/or specific orientation, with movements of the tool in said specific position and/or specific orientation resulting in movements of the selection pointer in the graphical user interface or interactions related to the triggered action.

It is pointed that the expression "database" as used hereinafter is referred to a collection of information recorded and organized in such as way so as to be retrievable by a processor. The expression "database" is therefore not limited by specific items of hardware.

DESCRIPTION OF THE PREFERRED EMBODIMENTS

Figure 1:
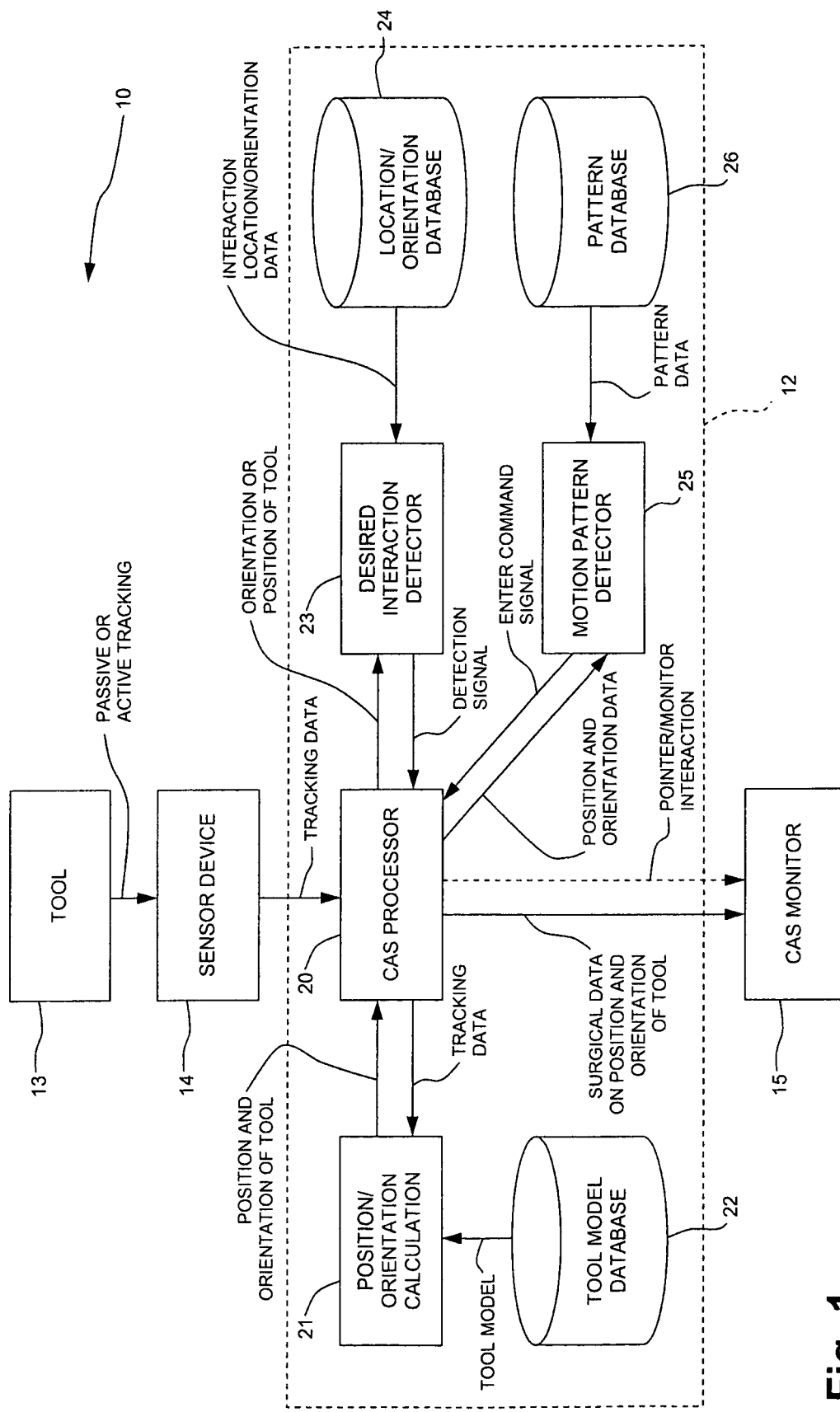
FIG. 1 is a block diagram of a user interface system for computer-assisted surgery in accordance with an embodiment of the present disclosure.

Referring now to the drawings, and more particularly to FIG. 1, a computer-assisted surgery (CAS) with user interface is generally shown at 10. The CAS system 10 has a CAS unit 12. The CAS unit 12 is a processing unit that calculates surgical data from the tracking of tools.

More specifically, the operator manipulates a tool 13 that is tracked by a sensor device 14. The sensor device 14 is connected to the CAS unit 12, whereby the CAS unit 12 receives tool tracking data from the sensor device 14. A CAS monitor 15 is also connected to the CAS unit 12, and outputs surgical data related to the position and/or orientation of the tool 13, in the form of visual representations, calculated values (e.g., distances, angles), amongst other possibilities.

The tracking of the tool 13 by the sensor device 14 uses active or passive detection. As a few non-exhaustive examples, the tracking involves optically-detectable retroreflective markers, accelerometers or gyroscopes with communication systems or RF tracking which are illustrated hereinafter. The user interface system 10 exclusively involves wireless tracking between the tool 13 and the sensor device 14.

The CAS unit 12 has a CAS processor 20 that receives and processes data received from the sensor device 14, and that outputs calculated surgical data to the CAS monitor 15. A position/orientation calculator 21 receives the tracking data from the sensor device 14, and calculates a position and orientation of the tool 13 from the tracking data. The calculation is performed by the position/orientation calculator 21 as a function of a calibration of the tool 13 executed initially, or as an optional alternative as a function of a model of the tool 13 as provided by the tool model database 22 (for instance the model being a geometric relation between a working tip of the tool 13 and a reference marker).

During surgery, the sterile zone often includes more than the limited area in which the surgery is effected. It is therefore desired to identify a location of the sterile zone located away from the bodily part being operated upon, namely a zone in which there is interaction between tool and bodily part. At this location, the tool 13 is selectively used as an interface with the CAS monitor 15 for the purposes of commanding the CAS system 10, in similar fashion to the use of a mouse to command a computer through a graphical user interface.

Accordingly, when the tool 13 reaches a given position, a desired interaction detector 23 associated with the CAS processor 20 identifies this action as a desired interaction from the operator. The desired interaction detector 23 typically identifies this action by comparing the tracked position of the tool 13 with location data stored in the location database 24. The location data can be obtained from an initial step of calibration in which an area is identified as user interface area. As a preferred embodiment, the location data is a specific tip position at which a tip of the tool 13 is positioned for interaction.

Figure 4:
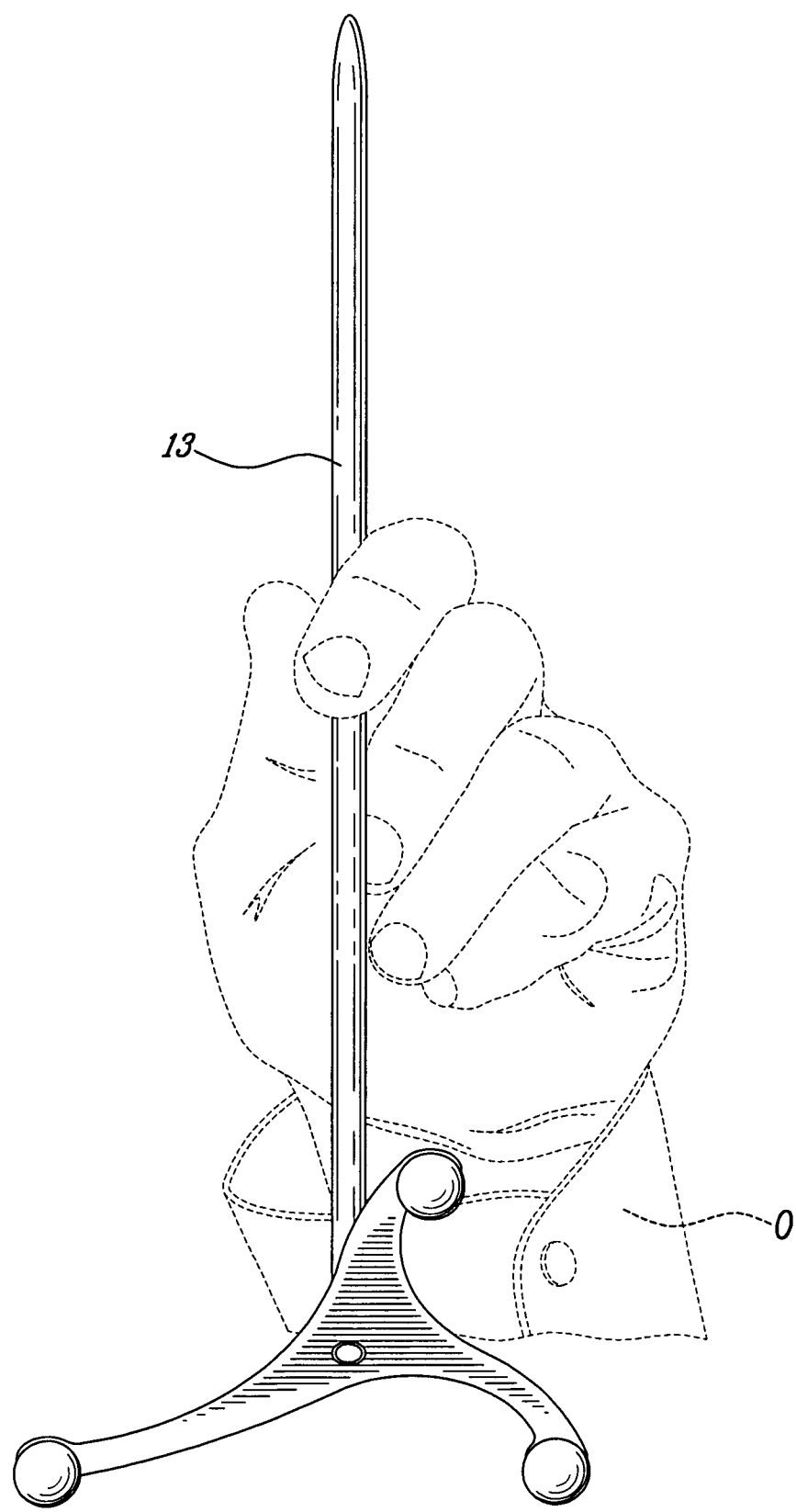
FIG. 4 is a schematic view of a surgical tool oriented for interaction with the user interface system of FIG. 1, in accordance with another embodiment.

As an alternative, when the tool 13 reaches a given orientation, the desired interaction detector 23 identifies this action as a desired interaction from the operator. For instance, as illustrated in FIG. 4, the given orientation comprises the operator orienting and maintaining the tool 13 in a generally upright orientation, with the tip of the tool 13 pointed upwardly and away from the body of the patient. The desired interaction detector 23 typically identifies this action by comparing the tracked orientation of the tool 13 with orientation data stored in the location/orientation database 24. In the case of a detection of orientation, the tool does not need to be brought to a specific zone of the sterile field for an interaction to be initiated.

Therefore, upon detecting a desired interaction from the position and/or orientation of the tool 13, the desired interaction detector 23 sends a detection signal to the CAS processor 20.

The CAS processor 20 therefore stops outputting surgical data pertaining to the position and orientation of the tool 13, and activates a selection pointer on the CAS monitor 15.

Thereafter, movements of the tool 13 within the selected position or orientation result in movements of the selection pointer on the screen of the CAS monitor 15. For instance, a lateral or a pivoting movement of the tool 13 in the upright orientation may result in a scrolling motion of the selection pointer, or in a change of application or task during the computer-assisted surgical procedure.

Additionally, a motion pattern detector 25 is provided to detect "enter" or "stop scrolling" signals from the interface tool 13. The motion pattern detector 25 is provided in association with the CAS processor 20, so as to receive position and orientation data pertaining to the tool 13, as provided by the CAS processor 20. The motion pattern detector 25 has a pattern database 26 to compare actual patterns of motion of the tool 13 with pattern data. Accordingly, the motion pattern detector 25 identifies specific motion patterns effected by the tool 13 as an "enter" command. In an embodiment, the tool 13 which was pivoted from its vertical position is simply returned to its vertical position.

Figure 2:
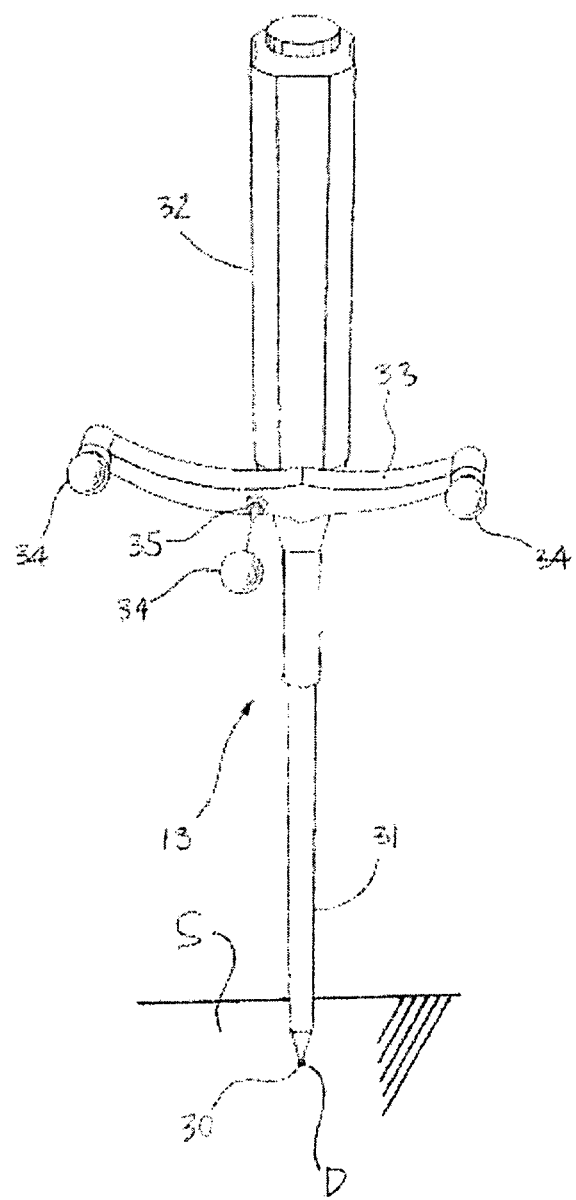
FIG. 2 is a perspective view of a surgical tool as used with the user interface system of FIG. 1, for interactions of an operator with a monitor.

Referring now to FIG. 2, one embodiment of the tool 13 is generally shown with respect to a surface S. It is pointed out that the tool 13 may take a plurality of forms. The tool 13 has a working tip 30 at an end of a working shaft 31 and a handle portion 32. A blade 33 is secured to the tool 13. More precisely, the blade 33 is positioned adjacent to the junction between the handle portion 32 and the working shaft 31. The blade 33 comprises detectable spheres 34. The spheres 34 are detachable from the blade 33, and are snap-fitted to connectors 35 (one shown) on the blade 33.

In the embodiment of FIG. 2, the detectable spheres 34 are each coated with a retroreflective layer in order to be detected by, for instance, an infrared sensor using axial illumination. It is pointed out that other shapes could be used as alternative embodiments to retroreflective spheres. As an example, straight cylinders, corner reflectors, flat geometric tokens or the like having retroreflective properties could also be used. It is preferred that the detectable devices be passive, such that they are wireless, but active wireless applications are known. For instance, it is possible to use active detectable devices, such as wireless magnetic sensors.

In a preferred embodiment using the registration pointer illustrated in FIG. 2, a divot D is provided in user interface area S. When the tip 30 of the tool 13 is positioned in the divot D, the CAS system 10 determines that an interaction of the user with the graphical user interface of the monitor 15 is desired. As mentioned previously, the CAS processor 20 (FIG. 1) therefore activates the selection pointer on the monitor 15.

As an alternative embodiment, it is considered to simply move the tool 13 to a portion of the sterile zone within the range of the sensor device 14, but distally positioned from the surgical field. For instance, a portion of the surgical table or the sterilized sheets covering the patient can be used as interface location.

Moreover, it is considered to have an interface location on the screen of the CAS monitor 15. As an image of the tool 13 (i.e., surgical data) moves on the screen of the CAS monitor 15 as a result of tracking of the tool 13, the image can be brought to the interface location on the screen by manipulation of the tool 13, to switch from surgical data to pointer mode. A reverse movement or other operation can return the tracking to surgical data mode.

Thereafter, movements of the tool 13 within the user interface area A are converted to movements of the selection pointer on the monitor 15. As the tip 30 is maintained in the divot D, it is suggested to use the registration pointer 13 as a joystick, with the tip 30/divot D as center of rotation for all movements of the tool 13.

The motion pattern for the tool 13 of FIG. 2 may be a quick up-and-down motion of the tool 13, with the tip 30 temporarily separated from the divot D, for the user to perform an "enter" or "select" command, equivalent to a click on a mouse. This motion pattern of the tool 13 can be used when the desired interaction detector 23 detects an orientation of the tool 13 (or a position and an orientation of the tool 13) as a desired interaction.

The motion pattern for the tool 13 of FIG. 2 may also be an axial rotation of the tool 13 indicating to the CAS system 10 that the operator has selected a value (i.e., equivalent to an "enter" command). A "scroll and select" action can be performed as well by combining motion patterns and movements of the tool 13.

As an alternative, the interface tool 13 as described previously is combined with a foot pedal that will be used to enter commands, for instance when the selection pointer is on an item in the graphical user interface of the monitor 15.

Figure 3:
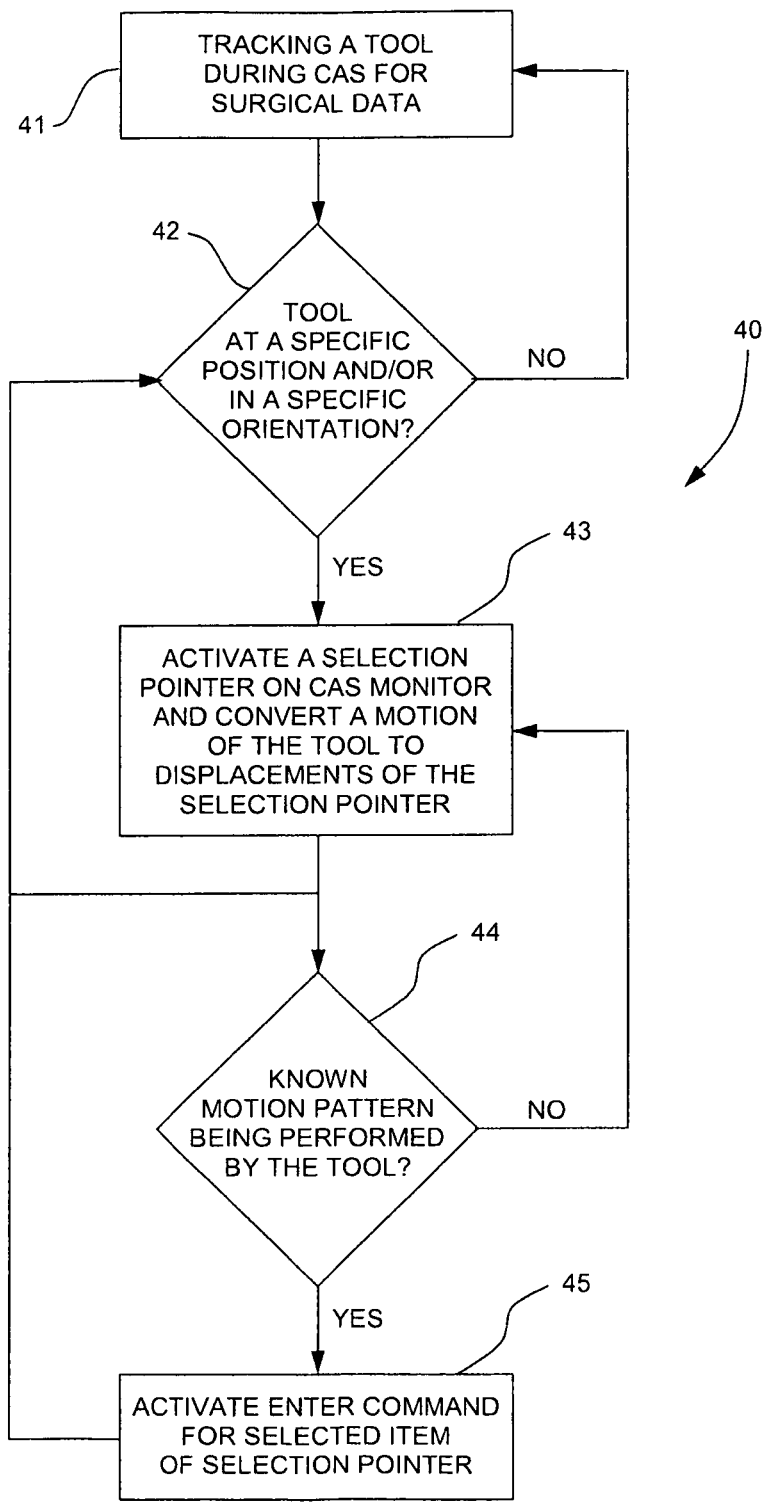
FIG. 3 is a flowchart illustrating a method of establishing an interaction between an operator and CAS monitor using tool tracking, in accordance with another embodiment of the present disclosure.

Referring to FIG. 3, a method for establishing an interaction between an operator and a CAS monitor, using for instance the CAS system 10, is generally shown at 10.

In Step 41, a tool is tracked for position and orientation using wireless tracking technology. The position and orientation data is used by a CAS system to calculate surgical data, such as angles, distances, etc.

In Decision 42, the position and/or the orientation of the tool is monitored, such that an action is triggered when the tool reaches the specific position (FIG. 2) and/or the specific orientation (FIG. 4).

In Step 43, once the specific position and/or the specific orientation has been reached, the action is that a selection pointer is activated on the CAS monitor, and a motion of the tool within the specific position is converted to displacements of the selection pointer on the CAS monitor.

Step 43 is performed while the tool is within the specific position and/or the specific orientation.

In Decision 44, the motion patterns of the tool are monitored, such that an action is triggered when the tool effects a specific motion pattern.

In Step 45, once the specific motion pattern has been recognized, the action is that an "enter" command is activated, for an item selected by the selection pointer.

The invention claimed is:

1. A method for establishing an interaction between an operator and a monitor of a computer-assisted surgery (CAS) system, comprising:
    visually tracking with a sensor device of the CAS system a surgical tool manipulated by the operator to perform a surgical task on a bone, the tracking providing surgical data calculated from a position and an orientation of the surgical tool;
    visually identifying a desire for mouse use from the operator to interact with the CAS system by tracking with the CAS system the surgical tool reaching a specific orientation from the visual tracking with the sensor device, irrespective of a position of the surgical tool;
    switching the CAS system from tracking the position of the surgical tool to tracking the surgical tool acting as a mouse upon the surgical tool being in the specific orientation, the specific orientation of the surgical tool activating an interactive action of the mouse on a monitor of the CAS system, the interactive action being unrelated to said surgical data; and
    using the surgical tool as the mouse by converting a visually tracked motion of the surgical tool with the CAS system to mouse interactions on the monitor.

2. The method according to claim 1, wherein activating an interactive action comprises activating a selection pointer on the monitor, and converting the visually tracked motion of the surgical tool comprises converting the visually tracked motion of the surgical tool to displacements of the selection pointer on the monitor, whereby the selection pointer moves on the monitor according to movements of the surgical tool as manipulated by the operator.

3. The method according to claim 2, wherein converting the visually tracked motion of the surgical tool to additional interactions comprises converting any one of pivoting motions and translational motions of the surgical tool to equivalent motions of the selection pointer on the monitor.

4. The method according to claim 2, wherein converting the visually tracked motion of the surgical tool further comprises converting a specific motion pattern of the surgical tool to an enter command associated with the position of the selection pointer on the monitor.

5. The method according to claim 1, wherein identifying the desire from the operator comprises tracking the surgical tool reaching a generally upright orientation with a tip of the surgical tool pointing upwardly.

6. The method according to claim 1, wherein using the surgical tool as a mouse comprises using the surgical tool only as a mouse upon a working tip of the surgical tool oriented to point away from a body of a patient and the surgical tool being incapable of performing the surgical task on the bone.

7. The method according to claim 1, wherein tracking to provide surgical data and tracking the surgical tool acting as a mouse is performed by the same sensor device.

8. The method according to claim 1, wherein switching the CAS system from tracking the position of the surgical tool to tracking the surgical tool comprises stopping providing said surgical data from the position and the orientation of the surgical tool.

9. The method according to claim 1, wherein visually detecting with the CAS system a motion pattern of the surgical tool includes comparing the detected motion pattern to a database of motion patterns each having an associated command, and activating one of a plurality of commands on the monitor upon the detected motion pattern matching a stored motion pattern associated with said command.

10. The method according to claim 1, further comprising visually detecting with the CAS system a motion pattern of the surgical tool used as the mouse, the surgical tool used as the mouse activating a command on the monitor upon the detected motion pattern matching a stored motion pattern associated with said command.

11. A computer-assisted surgery system comprising:
    a surgical tool having a trackable reference so as to be tracked for position, the surgical tool configured to perform a surgical task on a bone and configured to be used as a mouse;
    a sensor device configured to visually track the surgical tool;
    a computer-assisted surgery processing unit having:
        a position/orientation calculator in operation configured to at least an orientation of the surgical tool, the processing unit outputting surgical data as a function of at least the orientation of the surgical tool;
        a desired interaction detector configured to monitor the orientation of the surgical tool from visual tracking by the sensor device, the desired interaction detector switching the computer-assisted surgery system from tracking for outputting surgical data to tracking of the mouse by sending a detection signal based on a user's desire for mouse use to the processing unit to use the surgical tool as the mouse when the surgical tool is visually tracked in at least a specific orientation;

and a monitor for displaying a graphical user interface, the graphical user interface activating a selection pointer or triggering an action unrelated to said surgical data when the surgical tool is in said specific orientation irrespective of a position of the surgical tool, movements of the surgical tool as the mouse in said specific orientation resulting in movements of the selection pointer in the graphical user interface or interactions related to the triggered action.

12. The computer-assisted surgery system according to claim 11, wherein the specific orientation detected by the desired interaction detector comprises a generally upright orientation of the surgical tool, with a tip of the surgical tool pointing upwardly.

13. The computer-assisted surgery system according to claim 11, wherein the specific orientation detected by the desired interaction detector is defined by a working tip of the surgical tool pointing away from a body of a patient so as to be incapable of performing the surgical task in the specific orientation.

14. The computer-assisted surgery system according to claim 11, wherein the same sensor device is configured to track the surgical tool for outputting surgical data and for use as the mouse.

15. The computer-assisted surgery system according to claim 11, wherein the desired interaction detector is configured to stop outputting said surgical data of the surgical tool when switching the computer-assisted surgery system from tracking for outputting surgical data to tracking of the mouse.

16. The computer-assisted surgery system according to claim 11, wherein the motion pattern detector compares the detected motion pattern to a plurality of motion patterns in a database each having an associated command, and activating one of a plurality of commands on the monitor upon the detected motion pattern matching a stored motion pattern associated with said command.

17. The computer-assisted surgery system according to claim 11, further comprising a motion pattern detector communicating with a database of at least one motion pattern and associated command, the motion pattern detector configured to receive position and orientation data of the surgical tool from the sensor device to define a detected motion pattern of the surgical tool when used as the mouse, the motion pattern detector activating one command upon the detected motion pattern matching a motion pattern from the database associated with said command.

* * * * *